United States Patent [19]

Leinert et al.

[11] Patent Number: 4,937,337
[45] Date of Patent: Jun. 26, 1990

[54] SUBSTITUTED HETEROCYCLIC COMPOUNDS AND THE PHARMACOLOGICALLY ACCEPTABLE SALTS THEREOF, PROCESSES FOR THE PREPARATION THEREOF AND PHARMACEUTICAL COMPOSITIONS CONTAINING THEM

[75] Inventors: Herbert Leinert, Heppenheim; Christos Tsaklakidis, Weinheim; Peter Freund, Ketsch, all of Fed. Rep. of Germany

[73] Assignee: Boehringer Mannheim GmbH, Mannheim, Fed. Rep. of Germany

[21] Appl. No.: 322,025

[22] Filed: Mar. 10, 1989

[30] Foreign Application Priority Data

Mar. 10, 1988 [DE] Fed. Rep. of Germany ....... 3807922

[51] Int. Cl.$^5$ ................. C07D 295/00; C07D 265/36; C07D 265/30; C07D 209/02
[52] U.S. Cl. ..................................... 514/211; 544/105; 544/173; 544/353; 544/58.5; 514/224.2; 514/228.2; 514/233.8; 514/213; 514/215; 514/221; 514/230.5; 540/552; 546/159; 548/465
[58] Field of Search .............. 544/105, 58.5, 173, 544/353, 51; 548/465; 540/552; 546/159, 165

[56] References Cited

U.S. PATENT DOCUMENTS

| 3,535,338 | 10/1970 | Krapcho | 540/552 |
| 3,632,805 | 1/1972 | Yamamoto | 548/465 |
| 3,953,469 | 4/1976 | Krapcho | 544/105 |
| 4,255,430 | 3/1981 | Köppe et al. | |

FOREIGN PATENT DOCUMENTS 0166591 6/1985 European Pat. Off. .
0229329 12/1986 European Pat. Off. .

*Primary Examiner*—Mukund J. Shah
*Assistant Examiner*—E. C. Ward
*Attorney, Agent, or Firm*—Armstrong, Nikaido, Marmelstein, Kubovcik & Murray

[57] ABSTRACT

The present invention provides compounds of the general formula:

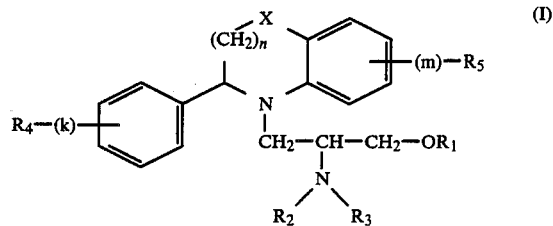

wherein $R_1$ is a straight-chained or branched $C_1$-$C_{12}$-alkyl radical which can be substituted by a phenyl, naphthyl or $C_3$-$C_7$-cycloalkyl radical, a straight-chained or branched $C_2$-$C_{12}$-alkenyl radical which can be substituted by a $C_3$-$C_7$-cycloalkyl, phenyl or naphthyl radical, a $C_3$-$C_7$-cycloalkyl radical or an unsubstituted or mono- or polysubstituted mono- or bicyclic aromatic radical, in which the substituents can be halogen atoms, carboxyl groups or $C_1$-$C_4$-alkyl, $C_1$-$C_4$-alkoxy or $C_1$-$C_4$-alkoxycarbonyl radicals, $R_2$ and $R_3$, which can be the same or different, are straight-chained, branched, saturated or unsaturated $C_1$-$C_6$-alkyl radicals or, together with the nitrogen atom to which they are attached, form a saturated or unsaturated ring which can contain further heteroatoms and can possibly be substituted by a $C_1$-$C_6$-alkyl radical, one or more $C_1$-$C_6$-alkoxy radicals, one or more hydroxyl groups or by an oxygen atom, X is a methylene radical, an oxygen or sulphur atom, a sulphoxide or sulphonyl group or an $=NR_6$ group, in which $R_6$ is a hydrogen atom or a $C_1$-$C_4$-alkyl or aralkyl radical, n is 0, 1 or 2, k is 0, 1, 2 or 3, $R_4$ is a halogen atom, a hydroxyl group or a $C_1$-$C_6$-alkyl, $C_1$-$C_6$-alkoxy or aralkoxy radical or, when k is 2, is a $C_1$-$C_2$-alkylenedioxy radical on two adjacent carbon atoms, m is 0, 1, 2 or 3 and $R_5$ is a halogen atom, a hydroxyl group or a $C_1$-$C_4$-alkyl, $C_1$-$C_6$-alkoxy or aralkoxy radical or, when m is 2, is a $C_1$-$C_2$-alkylenedioxy radical on two adjacent carbon atoms; as well as the pharmacologically acceptable salts thereof.

The present invention also provides processes for the preparation of these compounds and pharmaceutical compositions containing them.

20 Claims, No Drawings

SUBSTITUTED HETEROCYCLIC COMPOUNDS AND THE PHARMACOLOGICALLY ACCEPTABLE SALTS THEREOF, PROCESSES FOR THE PREPARATION THEREOF AND PHARMACEUTICAL COMPOSITIONS CONTAINING THEM

The present invention is concerned with substituted heterocyclic compounds and the pharmacologically acceptable salts thereof, processes for the preparation thereof and pharmaceutical compositions containing them.

The substituted heterocyclic compounds according to the present invention are compounds of the general formula:

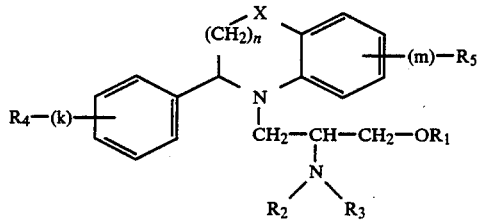

wherein $R_1$ is a straight-chained or branched $C_1$–$C_{12}$-alkyl radical which can be substituted by a phenyl, naphthyl, a $C_3$–$C_7$-cycloalkyl radical which may by substituted by $C_1$–$C_4$-alkyl, a straight-chained or branched $C_2$–$C_{12}$-alkenyl radical which can be substituted by a $C_3$–$C_7$-cycloalkyl, phenyl or naphthyl radical, a $C_3$–$C_7$-cyclo-alkyl radical or an unsubstituted or mono- or polysubstituted mono- or bicyclic aromatic radical, in which the substituents can be halogen atoms, carboxyl groups or $C_1$–$C_4$-alkyl, $C_1$–$C_4$-alkoxy or $C_1$–$C_4$-alkoxycarbonyl radicals, $R_2$ and $R_3$, which can be the same or different, are straight-chained, branched, saturated or unsaturated $C_1$–$C_6$-alkyl radicals or, together with the nitrogen atom to which they are attached, form a saturated or unsaturated ring which can contain further heteroatoms and can possibly be substituted by a $C_1$–$C_6$-alkyl radical, one or more $C_1$–$C_6$-alkoxy radicals, one or more hydroxyl groups or an oxygen atom, X is a methylene radical, an oxygen or sulphur atom, a sulphoxide or sulphonyl group or an $=NR_6$ group, in which $R_6$ is a hydrogen atom or a $C_1$–$C_4$alkyl or aralkyl radical, n is 0, 1 or 2, k is 0, 1, 2 or 3, $R_4$ is a halogen atom, a hydroxyl group or a $C_1$–$C_6$-alkyl, $C_1$–$C_6$-alkoxy or aralkoxy radical or, when k is 2, is a $C_1$–$C_2$-alkylenedioxy radical on two adjacent carbon atoms, m is 0, 1, 2 or 3 and $R_5$ is a halogen atom, a hydroxyl group or a $C_1$–$C_4$-alkyl, $C_1$–$C_6$-alkoxy or aralkoxy radical or, when m is 2, is a $C_1$–$C_2$-alkylenedioxy on two adjacent carbon atoms; as well as the pharmacologically acceptable salts and optical isomers thereof.

The $C_1$–$C_{12}$-alkyl radical $R_1$ is preferably a methyl, ethyl, propyl, isopropyl, n-butyl, isobutyl, isoamyl, isohexyl, n-hexyl, n-octyl or n-dodecyl radical and especially an isobutyl, isoamyl, isohexyl or neopentyl radical.

The $C_3$–$C_7$-cycloalkyl radical $R_1$ is, as a rule, a cyclopropyl, cyclopentyl or cyclohexyl radical, in which the cycloalkyl radical can also contain an additional alkyl radical, for example a methyl, ethyl or propyl radical.

When the alkyl radical is substituted, then preferred substituents include the cyclopentyl, cyclohexyl, phenyl and naphthyl radicals, in which the cyclopentyl and cyclohexyl radical can additionally contain an alkyl radical, for example a methyl, ethyl or propyl radical. Preferred is 1-methylcyclohexylmethyl.

The $C_2$–$C_{12}$-alkenyl radical $R_1$ is preferably an allyl, methallyl, isopentenyl, hexenyl, octenyl or dodecenyl radical, a substituted alkenyl radical being, for example, a cinnamyl radical.

If $R_1$ is a mono- or bicyclic aromatic radical, then this can be a phenyl, naphthyl, indanyl, indenyl or tetralinyl radical. In these, $C_1$–$C_4$-alkyl means a methyl, ethyl, propyl, isopropyl, butyl or tert.-butyl radical, $C_1$–$C_4$-alkoxy means a methoxy, ethoxy, propoxy, isopropoxy, butoxy or tert.-butoxy radical, halogen means a chlorine, bromine or fluorine atom and a $C_1$–$C_4$-alkoxycarbonyl radical is to be understood to include a methyl, ethyl, propyl, butyl or tert.-butyl ester.

$R_2$ and $R_3$ are preferably methyl, ethyl, propyl, allyl and methallyl radicals. Rings which $R_2$ and $R_3$ form together with the nitrogen atom to which they are attached are preferably a pyrrolidine, pyrroline or piperidine ring and especially a pyrrolidine ring. The heteroatoms which the rings can contain are nitrogen, sulphur and oxygen atoms. Hereunder are to be understood rings such as piperazine, morpholine and thiomorpholine. Substituents of the above-mentioned rings are especially hydroxyl groups and $C_1$–$C_3$-alkyl and $C_1$–$C_3$-alkoxy radicals, for example methyl, ethyl, propyl, methoxy, ethoxy and propoxy. As a rule, the oxygen substituent, together with the carbon atom to which it is attached, represents a carbonyl group. Corresponding rings include, for example the pyrrolidinone and the piperidinone rings.

When $R_4$ is a halogen atom, this is to be understood to be a chlorine, bromine or fluorine atom. Alkyl means a $C_1$–$C_6$-alkyl radical and preferably a $C_1$–$C_4$-alkyl radical, for example methoxy, ethoxy, n-propoxy, isopropoxy, n-butoxy, isobutoxy or tert.-butoxy. By aralkoxy is preferably to be understood the benzyloxy radical. When k is the number 2 on neighbouring carbon atoms, then $R_4$ is to be understood to be a methylenedioxy or ethylenedioxy radical.

k is 0, 1, 2 or 3, which means that either no substituent is present or that the number of substituents can vary between 1 and 3, all possible combinations of the substituents being possible independently of one another. Preferred is 0 or 1.

When $R_5$ is a halogan atom, this is to be understood to be a chlorine, bromine or fluorine atom. As a rule, $C_1$–$C_4$-alkyl means methoxy, ethoxy, n-propoxy, isopropoxy, n-butoxy, isobutoxy or tert.-butoxy. By aralkoxy is preferably to be understood a benzyloxy radical. When m is the number 2 on neighbouring carbon atoms, $R_5$ is to be understood to be a methylenedioxy or ethylenedioxy radical.

m is 0, 1, 2 or 3, which means that either no substituent is present or that the number of substituents can vary between 1 and 3, all possible combinations of the substituents being possible independently of one another. Preferred is 0 or 1.

When $R_6$ is $C_1$–$C_4$-alkyl, this is to be understood to be a methyl, ethyl, propyl or butyl radical. Aralkyl means benzyl or phenethyl radical.

The new compounds of general formula (I) according to the present invention can be prepared in known manner in that (a) a compound of the general formula:

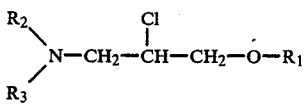 (II)

in which $R_1$, $R_2$ and $R_3$ have the above-given meanings, is reacted with a compound of the general formula:

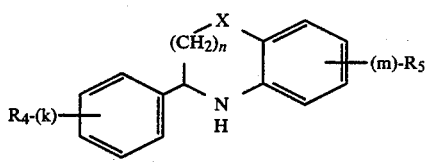 (III)

in which $R_4$, $R_5$, k, m and X have the above-given meanings, except that when the two symbols $R_2$ and $R_3$ together represent a ring substituted by one or two hydroxyl groups or when one of the symbols is a hydroxyl group, these are protected before the reaction and again split off after the reaction is completed, the protective groups used being, for example benzyloxy or methoxy-methyleneoxy radicals, or (b) a compound of the general formula:

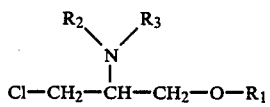 (IV)

in which $R_1$, $R_2$ and $R_3$ have the above-given meanings, is reacted with a compound of general formula (III), the same exceptions applying as in (a), or (c) a compound of the general formula:

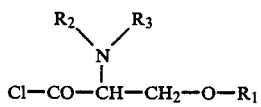 (V)

in which $R_1$, $R_2$ and $R_3$ have the above-given meanings, is reacted with a compound of general formula (III) and the compound obtained of the general formula:

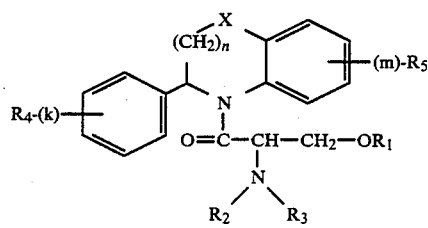 (VI)

in which $R_1$, $R_2$, $R_3$, $R_4$, $R_5$, X, k, m and n have the above-given meanings, is subjected to a reduction with a complex hydride.

The reaction of a compound of general formula (II) with a compound of general formula III to give a compound of general formula (I) according to the present invention takes place in known manner in an inert solvent, for example toluene, xylene or dimethylformamide, at a temperature of from 40° C. and the reflux temperature of the solvent in the presence of an alkaline condensation agent, for example sodium hydride or sodamide.

The compounds of general formula (II) can be prepared by reacting a compound of the general formula:

 (VII)

which $R_1$ has the above-given meaning, with epichlorohydrin in the presence of an aqueous solution of sodium hydroxide and of a phase transfer catalyst, for example tetrabutylammonium bromide, at a temperature of from ambient temperature to 50° C. and the compound obtained of the general formula:

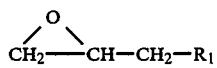 (VIII)

in which $R_1$ has the above-given meaning, is reacted in known manner with an amine of the general formula:

 (IX)

in which $R_2$ and $R_3$ have the above-given meanings, in a solvent, for example ethanol or propanol, at a temperature of from ambient temperature to the reflux temperature of the solvent and the compound obtained of the general formula:

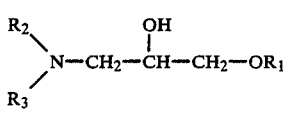 (X)

in which $R_1$, $R_2$ and $R_3$ have the above-given meanings, is reacted in an inert solvent, for example dichloroethane, with a chlorination agent, for example thionyl chloride, to give a compound of general formula (II).

The reaction of a compound of general formula (IV) with a compound of general formula (III) to give a compound of general formula (I) according to the present invention takes place in an inert solvent, for example toluene, xylene or dimethylformamide, at a temperature of from 40° C. to the reflux temperature of the solvent in the presence of an alkaline condensation agent, for example sodium hydride or sodamide.

The compounds of general formula (IV) can be prepared by reducing a compound of the general formula:

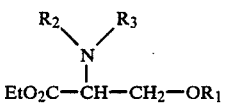 (XI)

in which $R_1$, $R_2$ and $R_3$ have the above-given meanings, with a complex hydride, for example lithium aluminium hydride, in an inert solvent, for example diethyl ether or tetrahydrofuran, in known manner to give a compound of the general formula:

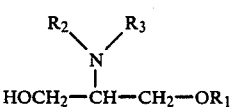 (XII)

in which $R_1$, $R_2$ and $R_3$ have the above-given meanings, and this is reacted in an inert solvent, for example dichloroethane, with a chlorination agent, for example thionyl chloride, to give a compound of general formula (IV).

The starting compounds of general formula (XI) can be prepared according to one of the processes described in Federal Republic of Germany Patent Specification No. 28 02 864.

The reaction of compounds of general formula (V) with compounds of general formula (III) to give a compound of general formula (VI) takes place according to processes known from the literature in an inert solvent, for example methylene chloride, in the presence of an acid-binding agent, for example triethylamine or pyridine. The reduction of a compound of general formula VI) to give a compound of general formula (I) according to the present invention takes place in an inert solvent, for example diethyl ether or tetrahydrofuran, with a complex hydride, for example lithium aluminium hydride.

The compounds of general formula (V) can be prepared by subjecting a compound of general formula (XI) to a hydrolysis and the compound obtained of the general formula:

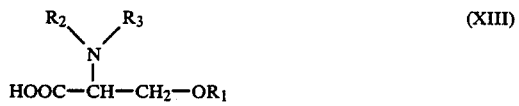

(XIII)

in which $R_1$, $R_2$ and $R_3$ have the above-given meanings, is reacted with a halogenation agent in an inert solvent, for example methylene chloride, dichloroethane or benzene.

The alcohols of the general formula (VII) used as starting materials are either commercially available or described in the literature.

The amines of the general formula (IX) are also commercially available or described in the literature.

The compounds of general formula (III) are described in the literature.

The compounds of general formula I) according to the present invention possess asymmetric carbon atoms. Therefore, the subject matter of the present invention also includes diastereomeric mixtures and all optically-active forms of the compounds of general formula (I) according to the present invention.

The separation of the diastereomeric mixtures takes place, for example, by chromatographic methods on a silica gel column. The subsequent separation of the enantiomeric mixtures takes place by known methods via diastereomeric salts. Optically-active acids which can be used for the racemate splitting include, for example, tartaric acid, malic acid, camphoric acid, camphorsulphonic acid and dibenzoxyltartaric acid.

For the conversion of compounds of general formula (I) into the pharmacologically acceptable salts thereof, these are reacted, preferably in an organic solvent, with an equivalent amount of an inorganic or organic acid, for example hydrochloric acid, hydrobromic acid, phosphoric acid, sulphuric acid, acetic acid, salicylic acid, citric acid, benzoic acid, naphthoic acid, o-acetoxybenzoic acid, adipic acid, maleic acid or oxalic acid.

The compounds of general formula (I) according to the present invention possess valuable pharmacological properties. They are especially characterised by a blood vessel-relaxing action and can, therefore, be used for the therapy of heart/circulatory diseases.

The new compounds of general formula (I) according to the present invention can be administered enterally or parenterally in liquid or solid form. As injection medium, it is preferred to use water which contains the additives usual in the case of injection solutions, such as stabilising agents, solubilising agents and/or buffers. Such additives include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, the state of health and the weight of the recipient, the extent of the disease, the nature of possibly simultaneously carried out further treatments, the frequency of the treatments and the nature of the desired action. An appropriate daily dosage of the active compounds is from 0.01 to 50 mg./kg. of body weight. This can be administered in appropriate dosage units one or more times per day.

Besides the compounds described in the Examples, the following compounds are also preferred according to the present invention:

1-[3-(2-methylpropoxy)-2-(3-hydroxypyrrolidino)-propyl]-2-phenylindoline

1-[3-(2-methylpropoxy)-2-(3,4-dihydroxypyrrolidino)-propyl]-2-phenylindoline

1-[3-(2-methylpropoxy)-2-(3-methoxypyrrolidino)-propyl]-2-phenylindoline

1-[3-(2-methylpropoxy)-2-(3,4-dimethoxypyrrolidino)-propyl]-2-phenylindoline 3,4-dihydro-4-[3-(2-methylprop-2-enyl-1-oxy)-2-(3-hydroxypyrrolidino)-propyl]-3-phenyl-2H-1,4-benzoxazine 3,4-dihydro-4-[3-(2-methylprop-2-enyl-1-oxy)-2-(3-methoxypyrrolidino)-propyl]-3-phenyl-2H-1,4-benzoxazine 3,4-dihydro-4-[3-(2-methylprop-2-enyl-1-oxy)-2-(3,4-dimethoxypyrrolidino)-propyl]-3-phenyl-2H-1,4benzoxazine 3,4-dihydro-4-[3-(3-methylprop-2-enyl-1-oxy)-2-(3-methoxypyrrolidino)-propyl]-3-phenyl-2H-1,4-benzoxazine 3,4-dihydro-4-[3-(3-methylbut-2-enyl-1-oxy)-2-(3,4-dimethoxypyrrolidino)-propyl]-3-phenyl-2H-1,4benzoxazine 1-[3-(3-methylbut-3-enyl-1-oxy)-2-(3-hydroxypyrrolidino)-propyl]-2-phenyl-1,2,3,4-tetrahydroquinoline 1-[3-(3-methylbut-3-enyl-1-oxy)-2-(3,4-dihydroxypyrrolidino)-propyl]-2-phenyl-1,2,3,4-tetrahydroquinoline 1-[3-(3-methylbut-3-enyl-1-oxy)-2-(3-methoxypyrrolidino)-propyl]-2-phenyl-1,2,3,4-tetrahydroquinoline 1-[3-(3-methylbut-3-enyl-1-oxy)-2-(3,4-dimethoxypyrrolidino)-propyl]-2-phenyl-1,2,3,4-tetrahydroquinoline 3,4-dihydro-4-[3-(2-methylbut-3-enyl-2-oxy)-2-(3-hydroxypyrrolidino)-propyl]-3-phenyl-2H-1,4-benzoxazine 3,4-dihydro-4-[3-(2-methylbut-3-enyl-2-oxy)-2-(3,4-dihydroxypyrrolidino)-propyl]-3-phenyl-2H-1,4benzoxazine 3,4-dihydro-4-[3-(2-methylbut-3-enyl-2-oxy)-2-(3-methoxypyrrolidino)-propyl]-3-phenyl-2H-1,4-benzoxazine 3,4-dihydro-4-[3-(2-methylbut-3-enyl-2-oxy)-2-(3,4-dimethoxypyrrolidino)-propyl]-3-phenyl-2H-1,4benzoxazine 1-[3-((1-methylcyclohexyl)-methoxy)-2-(3-methoxypyrrolidino)-propyl]-4-methyl-2-phenyl-1,2,3,4-tetrahydro-1,4-benzodiazine 1-[3-((1-methylcyclohexyl)-methoxy)-2-(3,4-dimethoxypyrrolidino)-propyl]-4-methyl-2-phenyl-1,2,3,4-tetrahydro-1,4-benzodiazine 3,4-dihydro-4-[3-(2,2-dimethylpropoxy)-2-(3-hydroxypyrrolidino)-propyl]-3-phenyl-2H-1,4-benzothiazine 3,4-dihydro-4-[3-(2,2-dimethylpropoxy)-2-(3-methoxypyrrolidino)-propyl]-3-phenyl-2H-1,4-benzothiazine 3,4-dihydro-4-[3-(2,2-dimethylpropoxy)-2-(3,4-dimethoxypyrrolidino)-propyl]-3-phenyl-2H-1,4-benzothiazine 3,4-dihydro-4-[3-(3-methylbutyl-1-oxy)-2-pyrrolidinopropyl]-3-phenyl-2H-1,4-benzoxazine 3,4-dihydro-4-[3-(4-methylpentyl-1-oxy)-2-pyrrolidinopropyl]-3-phenyl-2H-1,4-benzoxazine 3,4-dihydro-4-[3-(3-methylbutyl-1-oxy)-2-(3-methoxypyrrolidino)-propyl]-3-phenyl-2H-1,4-benzoxazine 3,4-dihydro-4-[3-(3-methylbutyl-1-oxy)-2-(3,4-dimethoxypyrrolidino)-propyl]-3-phenyl-2H-1,4-benzoxazine 3,4-dihydro-4-[3-(3-methylbutyl-1-oxy)-2-diethylaminopropyl]-3-phenyl-2H-1,4-benzoxazine 3,4-dihydro-4-[3-(4-methylpentyl-1-oxy)-2-diethylaminopropyl]-3-phenyl-2H-1,4-benzoxazine 3,4-dihydro-4-[3-(3-methylbutyl-1-oxy)-2-pyrrolidinopropyl]-3-phenyl-2H-1,4-benzothiazine 1-[3-(4-methylpentyl-1-oxy)-2-pyrrolidinopropyl]-2-phenyl-1,2,3,4-tetrahydroquinoline 1-[3-(3-methylbutyl-1-oxy)-2-diethylaminopropyl]-2-phenyl-1,2,3,4-tetrahydroquinoline 3,4-dihydro-4-[3-(3-methylbutyl-1-oxy)-2-diethylaminopropyl]-3-phenyl-2H-1,4-benzothiazine 1-(3-phenoxy-2-pyrrolidinopropyl)-2-phenylindoline 3,4-dihydro-4-(3-phenoxy-2-pyrrolidinopropyl)-3-phenyl-2H-1,4-benzoxazine 3,4-dihydro-4-[3-(4-methoxyphenoxy)-2-diethylaminopropyl]-3-phenyl-2H-1,4-benzoxazine 3,4-dihydro-4-[3-(4-methoxyphenoxy)-2-pyrrolidinopropyl]-3-(4-methoxyphenyl)-2H-1,4-benzoxazine 3,4-dihydro-4-[3-(4-methoxyphenoxy)-2-(3-methoxypyrrolidino)-propyl]-3-(4-methoxyphenyl)-2H-1,4benzoxazine 3,4-dihydro-4-[3-(4-methoxyphenoxy)-2-(3,4-dimethoxypyrrolidino)-propyl]-3-(4-methoxyphenyl)-7-methoxy-2H-1,4-benzoxazine 1-(3-benzyloxy-2-pyrrolidinopropyl)-2-phenylindoline 3,4-dihydro-4-(3-benzyloxy-2-pyrrolidinopropyl)-3-phenyl-2H-1,4-benzoxazine 3,4-dihydro-4-(3-benzyloxy-2-pyrrolidinopropyl)-3-phenyl-2H-1,4-benzothiazine 3,4-dihydro-4-[3-(4-methoxybenzyloxy)-2-diethylaminopropyl]-3-phenyl-2H-1,4-benzoxazine 3,4-dihydro-4-[3-(4-methoxybenzyloxy)-2-diethylaminopropyl]-3-(4-methoxyphenyl)-2H-1,4-benzoxazine 3,4-dihydro-4-(3-phenoxy-2-pyrrolidinopropyl)-3-(3-chlorophenyl)-2H-1,4-benzothiazine 1-(3-phenoxy-2-pyrrolidinopropyl)-2-(4-methylphenyl)-1,2,3,4-tetrahydroquinoline 1-(3-phenoxy-2-pyrrolidinopropyl)-2-(3,4-dimethoxyphenyl)-indoline 3,4-dihydro-4-(3-benzyloxy-2-pyrrolidinopropyl)-3-(4-methoxyphenyl)-2H-1,4-benzoxazine 3,4-dihydro-4-(3-benzyloxy-2-diethylaminopropyl)-3-(4-methoxyphenyl)-2H-1,4-benzoxazine 3,4-dihydro-4-(3-benzyloxy-2-pyrrolidinopropyl)-3-(3-chlorophenyl)-2H-1,4-benzothiazine 1-(3-benzyloxy-2-pyrrolidinopropyl)-2-(3,4-dimethoxyphenyl)-indoline 3,4-dihydro-4-[3-(2-phenylethoxy)-2-diethylaminopropyl]-3-phenyl-2H-1,4-benzoxazine 3,4-dihydro-4-[3-(3-phenylethoxy)-2-pyrrolidinopropyl]-3-phenyl-2H-1,4-benzoxazine 3,4-dihydro-4-[3-(3-phenylprop-2-enyl-1-oxy)-2-diethylaminopropyl]-3-phenyl-2H-1,4-benzoxazine 3,4-dihydro-4-[3-(3-phenylprop-2-enyl-1-oxy)-2-pyrrolidinopropyl]-3-phenyl-2H-1,4-benzoxazine 3,4-dihydro-4-[3-(3-phenylprop-2-enyl-1-oxy)-2-diethylaminopropyl]-3-(4-methoxyphenyl)-2H-1,4-benzoxazine 3,4-dihydro-4-[3-(3-phenylprop-2-enyl-1-oxy)-2-pyrrolidinopropyl]-3-(4-methoxyphenyl)-2H-1,4-benzoxazine 3,4-dihydro-4-[3-(2-methylpropoxy)-2-pyrrolidinopropyl]-3-(3,4-methylenedioxyphenyl)-2H-1,4-benzoxazine 3,4-dihydro-4-[3-(2-methylpropoxy)-2-pyrrolidinopropyl]-3-(4-methoxyphenyl)-2H-1,4-benzothiazine 1-[3-(2-methylpropoxy)-2-pyrrolidinopropyl]-2-(4-methoxyphenyl)-4-methoxyindoline 3,4-dihydro-4-[3-(2-methylpropoxy)-2-pyrrolidinopropyl]-3-(3,4-dimethoxyphenyl)-2H-1,4-benzoxazine 3,4-dihydro-4-[3-(2-methylpropoxy)-2-diethylaminopropyl]-3-(3,4-dimethoxyphenyl)-2H-1,4-benzoxazine 3,4-dihydro-4-[3-(2-methylprop-2-enyl-1-oxy)-2-pyrrolidinopropyl]-3-(3,4-dimethoxyphenyl)-2H-1,4-benzoxazine 3,4-dihydro-4-[3-(2-methylprop-2-enyl-1-oxy)-2-diethylaminopropyl]-3-(3,4-dimethoxyphenyl)-2H-1,4-benzoxazine 3,4-dihydro-4-[3-(2-methylprop-2-enyl-1-oxy)-2-(3-methoxypyrrolidino)-propyl]-3-(3,4-dimethoxyphenyl)-2H-1,4-benzoxazine 3,4-dihydro-4-[3-(2-methylpropoxy)-2-pyrrolidinopropyl]-3-(4-fluorophenyl)-2H-1,4-benzoxazine 3,4-dihydro-4-[3-(2-methylprop-2-enyl-1-oxy)-2-pyrrolidinopropyl]-3-(4-fluorophenyl)-2H-1,4-benzoxazine 3,4-dihydro-4-[3-(2,2-dimethylpropoxy)-2-diethylaminopropyl]-3-(4-fluorophenyl)-2H-1,4-benzoxazine 3,4-dihydro-4-[3-((1-methylcyclohexyl)-methoxy)-2-(3-hydroxypyrrolidino)-propyl]-3-(4-fluorophenyl)-2H-1,4-benzoxazine 3,4-dihydro-4-[3-(2-methylpropoxy)-2-pyrrolidinopropyl]-3-(3,4,5-trimethoxyphenyl)-2H-1,4-benzoxazine 3,4-dihydro-4-[3-(2-methylprop-2-enyl-1-oxy)-2-diethylaminopropyl]-3-(3,4,5-trimethoxyphenyl)-2H-1,4-benzoxazine 3,4-dihydro-4-[3-(2-methylbut-3-enyl-2-oxy)-2-pyrrolidinopropyl]-3-(3,4,5-trimethoxyphenyl)-2H-1,4-benzoxazine 3,4-dihydro-4-[3-(2-methylpropoxy)-2-pyrrolidinopropyl]-3-(3-methoxyphenyl)-2H-1,4-benzoxazine 3,4-dihydro-4-[3-(2-methylprop-2-enyl-1-oxy)-2-pyrrolidinopropyl]-3-(2-methoxyphenyl)-2H-1,4-benzoxazine 3,4-dihydro-4-[3-(3-methylbut-2-enyl-1-oxy)-2-diethylaminopropyl]-3-(2-methoxyphenyl)-2H-1,4-benzoxazine 3,4-dihydro-4-[3-(2,2-dimethylpropoxy)-2-(3-methoxypyrrolidino)-propyl]-3-(2-methoxyphenyl)-2H-1,4-benzoxazine 3,4-dihydro-4-[3-(2-methylpropoxy)-2-pyrrolidinopropyl]-3-(3-methoxyphenyl)-2H-1,4-benzoxazine 3,4-dihydro-4-[3-(2-methylprop-2-enyl-1-oxy)-2-pyrrolidinopropyl]-3-(3-methoxyphenyl)-2H-1,4-benzoxazine 3,4-dihydro-4-[3-(3-methylbut-2-enyl-1-oxy)-2-diethylaminopropyl]-3-(3-methoxyphenyl)-2H-1,4-benzoxazine 3,4-dihydro-4-[3-(2,2-dimethylpropoxy)-2-pyrrolidinopropyl]-3-(3-methoxyphenyl)-2H-1,4-benzoxazine 3,4-dihydro-4-[3-(2-methylpropoxy)-2-(3-methoxypyrrolidinopropyl]-3-(3-methoxyphenyl)-2H-1,4-benzoxazine 3,4-dihydro-4-[3-(2-methylprop-2-enyl-1-oxy)-2-(3-methoxypyrrolidinopropyl]-3-(3-methoxyphenyl)-2H-1,4-benzoxazine 3,4-dihydro-4-(3-phenoxy-2-pyrrolidinopropyl]-3-(3-methoxyphenyl)-2H-1,4-benzoxazine 3,4-dihydro-4-(3-benzyloxy-2-pyrrolidinopropyl)-3-(3-methoxyphenyl)-2H-1,4-benzoxazine 3,4-dihydro-4-[3-(2-phenylethoxy)-2-(3-methoxypyrrolidino)-propyl]-3-(3-methoxyphenyl)-2H-1,4-benzoxazine 3,4-dihydro-4-[3-(2-methylprop-2-enyl-1-oxy)-2-pyrrolidinopropyl]-3-(4-methoxyphenyl)-2H-1,4benzoxazine 3,4-dihydro-4-[3-(2-methylprop-2-enyl-1-oxy)-2-diethylaminopropyl]-3-(4-methoxyphenyl)-2H-1,4-benzoxazine 3,4-dihydro-4-[3-(2,2-dimethylpropoxy)-2-diethylaminopropyl]-3-(4-methoxyphenyl)-2H-1,4-benzoxazine 3,4-dihydro-4-[3-(2-methylprop-2-enyl-1-oxy)-2-morpholinopropyl]-3-(4-methoxyphenyl)-2H-1,4-benzoxazine 3,4-dihydro-4-[3-(2-methylbut-3-enyl-1-oxy)-2-diethylaminopropyl]-3-(4-methoxyphenyl)-2H-1,4-benzoxazine 3,4-dihydro-4-[3-(3-methylbut-2-enyl-1-oxy)-2-morpholinopropyl]-3-(4-methoxyphenyl)-2H-1,4-benzoxazine 3,4-dihydro-4-[3-(2-methylpropoxy)-2-piperidinopropyl]-3-(4-methoxyphenyl)-2H-1,4-benzoxazine 3,4-dihydro-4-[3-(2-methylpropoxy)-2-pyrrolidinopropyl]-3-(4-hydroxyphenyl)-2H-1,4-benzoxazine 3,4-dihydro-4-[3-(2-methylpropoxy)-2-(3-methoxypyrrolidino)-propyl]-3-(4-hydroxyphenyl)-2H-1,4-benzoxazine 3,4-dihydro-4-(3-phenoxy-2-diethylaminopropyl)-3-(4-hydroxyphenyl)-2H-1,4-benzoxazine 3,4-dihydro-4-(3-benzyloxy-2-morpholinopropyl)-3-(4-hydroxyphenyl)-2H-1,4-benzoxazine 3,4-dihydro-4-[3-(2-phenylethoxy)-2-piperidinopropyl)-3-(4-hydroxyphenyl)-2H-1,4-benzoxazine 3,4-dihydro-4- 3-(2-methylpropoxy)-2-pyrrolidinopropyl]-3-(4-allyloxyphenyl)-2H-1,4-benzoxazine 3,4-dihydro-4-(3-phenoxy-2-diethylaminopropyl)-3-(4-allyloxyphenyl)-2H-1,4-benzoxazine 3,4-dihydro-4-[3-(2-methylpropoxy)-2-piperidinopropyl]-3-(4-propoxyphenyl)-2H-1,4-benzoxazine 3,4-dihydro-4-[3-(2-methylpropoxy)-2-pyrrolidinopropyl]-3-(3,4-dimethoxyphenyl)-2H-1,4-benzothiazine 3,4-dihydro-4-[3-(2-methylprop-2-enyl-1-oxy)-2-pyrrolidinopropyl]-3-(3,4-dimethoxyphenyl)-2H-1,4-benzothiazine 3,4-dihydro-4-[3-(2-methylpropoxy)-2-diethylaminopropyl]-3-(4-fluorophenyl)-2H-1,4-benzothiazine 3,4-dihydro-4-[3-(2-methylprop-2-enyl-1-oxy)-2-pyrrolidinopropyl]-3-(3,4,5-trimethoxyphenyl)-2H-1,4-benzothiazine 3,4-dihydro-4-[3-(2-methylpropoxy)-2-pyrrolidinopropyl]-3-(3,4,5-trimethoxyphenyl)-2H-1,4-benzothiazine 3,4-dihydro-4-[3-(2-methylpropoxy)-2-diethylaminopropyl]-3-(2-methoxyphenyl)-2H-1,4-benzothiazine 3,4-dihydro-4-[3-(2-methylprop-2-enyl-1-oxy)-2-pyrrolidinopropyl]-3-(2-methoxyphenyl)-2H-1,4-benzothiazine 3,4-dihydro-4-(3-phenoxy-2-morpholinopropyl)-3-(2-methoxyphenyl)-2H-1,4-benzoxazine 3,4-dihydro-4-[3-(2-methylpropoxy)-2-pyrrolidinopropyl]-3-(3-methoxyphenyl)-2H-1,4-benzothiazine 3,4-dihydro-4-[3-(2-methylprop-2-enyl-1-oxy)-2-pyrrolidinopropyl]-3-(3-methoxyphenyl)-2H-1,4-benzothiazine 3,4-dihydro-4-[3-(2-methylprop-2-enyl-1-oxy)-2-diethylaminopropyl]-3-(3-methoxyphenyl)-2H-1,4-benzothiazine 3,4-dihydro-4-[3-(2,2-dimethylpropyloxy)-2-diethylaminopropyl]-3-(3-methoxyphenyl)-2H-1,4-benzothiazine 3,4-dihydro-4-[3-(2-methylprop-2-enyl-1-oxy)-2-diethylaminopropyl]-3-(4-methoxyphenyl)-2H-1,4-benzothiazine 3,4-dihydro-4-[3-(3-methylbut-2-enyl-1-oxy)-2-pyrrolidinopropyl]-3-(4-methoxyphenyl)-2H-1,4-benzothiazine 3,4-dihydro-4-[3-(3-methylbut-3-enyl-1-oxy)-2-pyrrolidinopropyl]-3-(4-methoxyphenyl)-2H-1,4-benzothiazine 3,4-dihydro-4-[3-(2-methylpropoxy)-2-pyrrolidinopropyl]-3-(4-hydroxyphenyl)-2H-1,4-benzothiazine 3,4-dihydro-4-[3-(2-methylpropoxy)-2-pyrrolidinopropyl]-3-(4-allyloxyphenyl)-2H-1,4-benzothiazine 3,4-dihydro-4-[3-(2-methylprop-2-enyl-1-oxy)-2-diethylaminopropyl]-3-(4-allyloxyphenyl)-2H-1,4-benzothiazine 3,4-dihydro-4-[3-(2-methylpropoxy)-2-pyrrolidinopropyl]-3-(4-propoxyphenyl)-2H-1,4-benzothiazine 3,4-dihydro-4-[3-(2-methylprop-2-enyl-1-oxy)-2-diethylaminopropyl]-3-(4-propoxyphenyl)-2H-1,4-benzothiazine 1-[3-(2-methylprop-2-enyl-1-oxy)-2-pyrrolidinopropyl]-2-(4-methoxyphenyl)-1,2,3,4-tetrahydroquinoline 1-[3-(2-methylprop-2-enyl-1-oxy)-2-diethylaminopropyl]-2-(4-methoxyphenyl)-1,2,3,4-tetrahydroquinoline 1-[3-(2,2-dimethylpropoxy)-2-pyrrolidinopropyl]-2-(4-methoxyphenyl)-1,2,3,4-tetrahydroquinoline 1-(3-phenoxy-2-pyrrolidinopropyl)-2-(4-methoxyphenyl)-1,2,3,4-tetrahydroquinoline 1-[3-(2-methylpropoxy)-2-(3-methoxypyrrolidino)-propyl]-2-(4-methoxyphenyl)-1,2,3,4-tetrahydroquinoline 1-[3-(2-methylprop-2-enyl-2-oxy)-2-(3-methoxypyrrolidino)-propyl]-2-(4-methoxyphenyl)-1,2,3,4-tetrahydroquinoline 1-[3-(3-methylbut-3-enyl-1-oxy)-2-pyrrolidinopropyl]-2-(4-methoxyphenyl)-1,2,3,4-tetrahydroquinoline 5-[3-(2-methylpropoxy)-2-pyrrolidinopropyl]-4-phenyl-2,3,4,5-tetrahydro-1,5-benzoxazepine 5-[3-(2-methylpropoxy)-2-diethylaminopropyl]-4-phenyl-2,3,4,5-tetrahydro-1,5-benzoxazepine 5-[3-(2-methylprop-2-enyl-1-oxy)-2-pyrrolidinopropyl]-4-phenyl-2,3,4,5-tetrahydro-1,5-benzoxazepine 5- 3-(2-methylpropoxy)-2-pyrrolidinopropyl]-4-(4-methoxyphenyl)₂2,3,4,5-tetrahydro-1,5-benzoxazepine 5-[3-(2-methylpropoxy)-2-diethylaminopropyl]-4-(4-methoxyphenyl)-2,3,4,5-tetrahydro-1,5-benzoxazepine 5-[3-(2-methylpropoxy)-2-pyrrolidinopropyl]-4-(4-methoxyphenyl)-8-methoxy-2,3,4,5-tetrahydro-1,5-benzoxazepine 5-[3-(2-methylpropoxy)-2-pyrrolidinopropyl]-4-(4-fluorophenyl)-2,3,4,5-tetrahydro-1,5-benzoxazepine 5-[3-(2-methylprop-2-enyl-1-oxy)-2-diethylaminopropyl]-4-(4-fluorophenyl)-2,3,4,5-tetrahydro-1,5-benzoxazepine 5-[3-(2,2-dimethylpropoxy)-2-diethylaminophenyl]-4-(4-fluorophenyl)-2,3,4,5-tetrahydro-1,5-benzoxazepine 5-[3-(2-methylbut-3-enyl-1-oxy)-2-pyrrolidinopropyl]-4-(4-fluorophenyl)-2,3,4,5-tetrahydro-1,5-benzoxazepine 5-[3-(2-methylpropoxy)-2-(3-methoxypyrrolidino)-propyl]-4-phenyl-2,3,4,5-tetrahydro-1,5-benzoxazepine 5-[3-(2-methylpropoxy)-2-(3-methoxypyrrolidino)-4-(4-methoxyphenyl)-2,3,4,5-tetrahydro-1,5-benzoxazepine 5-[3-(2-methylpropoxy -2-(3-methoxypyrrolidino)-4-(4-fluorophenyl)-2,3,4,5-tetrahydro-1,5-benzoxazepine 5-(3-phenoxy-2-pyrrolidinopropyl)-4-phenyl-2,3,4,5-tetrahydro-1,5-benzoxazepine 5-[3-(4-methoxyphenoxy)-2-(3-methoxypyrrolidino)-propyl]-4-(methoxyphenyl)-2,3,4,5-tetrahydro-1,5-benzoxazepine 5-[3-(4-methoxyphenoxy)-2-diethylaminopropyl -4-(4-methoxyphenyl)-2,3,4,5-tetrahydro-1,5-benzoxazepine 5-[3-(2-methylpropoxy)-2-pyrrolidinopropyl -4-phenyl-2,3,4,5-tetrahydro-1,5-benzothiazepine 5-[3-(2-methylpropoxy)-2-diethylaminopropyl]-4-phenyl-2,3,4,5-tetrahydro-1,5-benzothiazepine 5-[3-(2-methylprop-2-enyl-1-oxy)-2-pyrrolidinopropyl]-4-phenyl-2,3,4,5-tetrahydro-1,5-benzothiazepine 5-[3-(2,2-dimethylpropoxy)-2-pyrrolidinopropyl]-4-phenyl-2,3,4,5-tetrahydro-1,5-benzothiazepine 5-[3-(2,2-dimethylpropoxy)-2-(3-methoxypyrrolidino)-propyl]-4-phenyl-2,3,4,5-tetrahydro-1,5-benzothiazepine 5-[3-(2-methylbut-3-enyl-2-oxy)-2-diethylaminopropyl]-4-phenyl-2,3,4,5-tetrahydro-1,5-benzothiazepine 5-[3-(2-methylpropoxy)-2-pyrrolidinopropyl]-4-(4-methoxyphenyl)-2,3,4,5-tetrahydro-1,5-benzothiazepine 5-[3-(2-methylprop-2-enyl-1-oxy)-2-diethylaminopropyl]-4-(4-methoxyphenyl)-2,3,4,5-tetrahydro-1,5-benzothiazepine 5-[3-(2-methylpropoxy)-2-pyrrolidinopropyl]-4-(4-fluorophenyl)-2,3,4,5-tetrahydro-1,5-benzothiazepine 5-(3-phenoxy-2-pyrrolidinopropyl)-4-phenyl-2,3,4,5-tetrahydro-1,5-benzothiazepine 5-[3-(4-methoxyphenoxy)-2-(3-methoxypyrrolidino)-propyl]-4-(4-methoxyphenyl)-2,3,4,5-tetrahydro-1,5-benzothiazepine 5-[3-(4-methoxyphenoxy)-2-dimethylaminopropyl]-4-(4-methoxyphenyl)-2,3,4,5-tetrahydro-1,5-benzothiazepine.

The following Examples are given for the purpose of illustrating the present invention:

EXAMPLE 1

1-[3-(2-Methylpropoxy)-2-pyrrolidinopropyl]-2-phenylindoline.

4 g. 2-Phenylindoline are dissolved in 25 ml. dimethylformamide and the solution mixed with 1.2 g. sodium hydride (50% suspension in oil). The reaction mixture is heated, while stirring, to 80° C. until the evolution of hydrogen is finished. Thereafter, a solution of 4.5 g. 1-[2-chloro-2-(2-methylpropoxy)-propyl]pyrrolidine in 25 ml. dimethylformamide is added dropwise thereto in the course of 15 minutes and stirring continued for 3 hours at 80° C. The reaction mixture is cooled, mixed with water and extracted with methylene chloride. The methylene chloride phase is washed with water, dried over anhydrous sodium sulphate and evaporated. For purification, the residue is chromatographed on a silica gel column (elution agent: toluene/10% ethyl acetate). After evporation of the appropriate column fractions, there are obtained 3.5 g. of the title compound in the form of an oily product.

The following compounds are prepared analogously:

EXAMPLE 2

1-[3-(2-methylpropoxy)-2-pyrrolidinopropyl]-2-(4-methoxyphenyl)-indoline; oil, m/e 408.

EXAMPLE 3

3,4-Dihydro-4-[3-(2-methylpropoxy)-2-pyrrolidinopropyl]-3-phenyl-2H-1,4-benzoxazine oxalate; m.p. 159°–160° C.

EXAMPLE 4

3,4-Dihydro-4-[3-(2-methylpropoxy)-2-pyrrolidinopropyl]-3-(4-methoxyphenyl)-2H-1,4-benzoxazine; oil, m/e 424.

EXAMPLE 5

1-[3-(2-Methylpropoxy)-2-pyrrolidinopropyl]-2-phenyl-1,2,3,4-tetrahydroquinoline oxalate; m.p. 141°–142° C.

EXAMPLE 6

3,4-Dihydro-4-[3-(2-methyl-2-propenyl-1-oxy)-2-pyrrolidinopropyl]-3-phenyl-2H1,4-benzoxazine oxalate: m.p. 120°–121° C.

EXAMPLE 7

3,4-Dihydro-4-[3-(3-methylbut-2-enyl-1-oxy)-2-pyrrolidinopropyl]-3-phenyl-2H-1,4-benzoxazine; oil, m/e 406.

EXAMPLE 8

3,4-Dihydro-4-[3-(3-methyl-3-butenyl-1-oxy)-2-pyrrolidinopropyl]-3-phenyl-2H-1,4-benzoxazine; oil. m/e 406.

EXAMPLE 9

3,4-Dihydro-4-[3-((1-methylcyclohexyl)-methoxy)-2-pyrrolidinopropyl]-3-phenyl-2H-1,4-benzoxazine; oil, m/e 448.

EXAMPLE 10

3,4-Dihydro-4-[3-(2-methylpropoxy)-2-Pyrrolidinopropyl]-3-(4-methoxyphenyl)-7-methoxy-2H-1,4-benzoxazine; oil, m/e 454.

EXAMPLE 11

3,4-Dihydro-4-[3-(2,2-dimethylpropoxy)-2-pyrrolidinopropyl]-3-phenyl-2H-1,4-benzoxazine; oil, m/e 408

EXAMPLE 12

3,4-Dihydro-4-[3-(2-methylpropoxy)-2-pyrrolidinopropyl]-3-phenyl-2H-1,4-benzothiazine; oil, m/e 410.

EXAMPLE 13

3,4-Dihydro-4-[3-(2-methylbut-3-enyl-2-oxy)-2-pyrrolidinopropyl]-3-phenyl-2H-1,4-benzoxazine; oil, m/e 406.

EXAMPLE 14

1-[3-(2-Methylbut-3-enyl-2-oxy)-2-pyrrolidinopropyl]-2-phenyl-indoline; oil, m/e 390.

EXAMPLE 15

1-[3-(3-Methylbut-2-enyl-1-oxy)-2-pyrrolidinopropyl]-2-phenyl-indoline; oil, m/e 390.

EXAMPLE 16

1-[3-(3-Methylbut-3-enyl-1-oxy)-2-pyrrolidinopropyl]-2-phenylindoline; oil, m/e 390.

EXAMPLE 17

3,4-Dihydro-4-[3-(2-methylpropoxy)-2-diethylaminopropyl]-3-phenyl-2H-1,4-benzoxazine; oil, m/e 396.

EXAMPLE 18

3-(2-Methylpropoxy)-2-pyrrolidinopropyl]-4-methyl-2-phenyl-1,2,3,4-tetrahydro-1,4-benzodiazine; oil, m/e 407.

EXAMPLE 19

1-[3-(2-Methylpropoxy)-2-pyrrolidinopropyl]-2-(4-methoxyphenyl)-1,2,3,4-tetrahydroquinoline; oil, m/e 422.

EXAMPLE 20

3,4-Dihydro-4-(3-alloxy-2-pyrrolidinopropyl]-3-phenyl-2H-1 4-benzoxazine; oil: m/e 378.

For the characterisation of the compounds prepared, in many cases there is given the mass spectrometrically determined mol peak m/e.

Preparation of the Starting Materials

The preparation of 1-[2-chloro-3-(2-methylpropoxy)-propyl]-pyrrolidine is described as a representative example. The other starting materials required of general formula (II) are prepared in an analogous manner.

Step 1.

1-(2-Methylpropoxy)-Z,3-epoxypropane.

A mixture of 24.2 g. isobutanol, 85 ml. concentrated aqueous sodium hydroxide solution, 100 ml. epichlorohydrin and 2 g. tetrabutoxyammonium bromide is intensively stirred for 5 hours at 40° C. The reaction mixture is then cooled and poured into ice water and extracted with ethyl acetate. The ethyl acetate phase is separated off, dried over anhydrous sodium sulphate and evaporated. The residue is distilled in a vacuum. There are obtained 25 g. 1-(2-methylpropoxy)-2,3-epoxypropane; b.p. 75°–80° C./50 mm.Hg.

The following compounds are prepared in an analogous manner:
1-allyloxy-2,3-epoxypropane;
b.p. 78° C./56 mm.Hg.
1-(2-methylprop-2-enyl-1-oxy)-2,3-epoxypropane;
b.p. 84°–87° C./40 mm.Hg.
1-(3-methylbut-2-enyl-1-oxy)-2,3-epoxypropane;
b.p. 85–°87° C./13 mm.Hg.
1-(3-methylbut-3-enyl-1-oxy)-2,3-epoxypropane;
b.p. 77°–80° C./13 mm.Hg.
1-(2-methylbut-3-enyl-2-oxy)-2,3-epoxypropane;
b.p. 66°–70° C./13 mm.hg.
1-[(1-methylcyclohexyl)-methoxy]-2,3-epoxypropane;
b.p. 120°–125° C./13 mm.Hg.
1-(2,2-dimethylpropoxy)-2,3-epoxypropane;
b.p. 85°–86° C./50 mm.Hg.

Step 2.

3-(2-methoxypropoxy)-1-pyrrolidinopropan-2-ol.

20 g. 1-(2-Methylpropoxy)-2,3-epoxypropane are dissolved in 40 ml. ethanol and the solution is warmed to 55° C. Subsequently, in the course of an hour and while stirring, there is added dropwise a solution of 13 g. pyrrolidine in 25 ml. ethanol. The temperature should thereby not increase above 70° C. After completion of the addition, stirring is continued for 1 hour at 70° C., the reaction mixture is then evaporated and the residue is distilled in a vacuum. There are obtained 35 g. 3-(2-methylpropoxy)-1-pyrrolidinopropan-2-ol; b.p. 134° C./14 mm.Hg.

The following compounds are prepared in an analogous manner:
3-allyloxy-1-pyrrolidinopropan-2-ol;
b.p. 75° C./$10^{-2}$ mm./Hg.
3-(2-methylpropenyloxy)-1-pyrrolidinopropan-2-ol;
b.p. 94° C./$10^{-2}$ mm /Hg.
3-(2-methylbut-2-enyl-1-oxy)-1-pyrrolidinopropan-2-ol;
b.p. 94° C./$2.10^{-2}$ mm./Hg.
3-(3-methylbut-3-enyl-1-oxy)-1-pyrrolidinopropan-2-ol;
b.p. 108° C./$4.10^{-2}$ mm./Hg.
3-(2-methylbut-3-enyl-2-oxy)-1-pyrrolidinopropan-2-ol;
b.p. 80° C./$2.10^{-2}$ mm./Hg.
3-[(1-methylcyclohexyl)-1-pyrrolidinopropan-2-ol;
b.p. 107° C./$10^{-2}$ mm./Hg.
3-(2,2-dimethylpropoxy)-1-pyrrolidinopropan-2-ol;
b.p. 76° C./$10^{-2}$ mm./Hg.
3-(2-methylpropoxy)-1-diethylaminopropan-2-ol;
b.p. 80° C./1.5 mm./Hg.

Step 3.

10 g. 3-(2-Methylpropoxy)-1-pyrrolidinopropan-2-ol are dissolved in 100 ml. dichloroethane. A solution of 7.1 g. thionyl chloride in 20 ml. dichloroethane is added dropwise thereto, while stirring, and the reaction mixture subsequently heated for 2 hours to 70° C. The reaction mixture is cooled, poured on to ice water and subsequently rendered alkaline by the addition of a concentrated aqueous solution of sodium hydroxide. The organic phase is separated off and the aqueous phase again extracted with methylene chloride. The organic phases are combined, dried over anhydrous sodium sulphate and evaporated. The residue is purified by chromatography on a silica gel column (elution agent: methylene chloride/5% methanol). There are obtained 9 g. of the title compound in the form of an oily product.

The following compounds are prepared in an analogous manner:

1-(3-allyloxy-2-chloropropyl)-pyrrolidine
1-[2-chloro-(2-methylpropenyl-1-oxy)-propyl]-pyrrolidine
1-[2-chloro-(3-methylbut-2-enyl-1-oxy)-propyl]-pyrrolidine
1-[2-chloro-(3-methylbut-3-enyl-1-oxy)-propyl]-pyrrolidine
1-[2-chloro-(2-methylbut-3-enyl-1-oxy)-propyl]-pyrrolidine
1-[2-chloro-((1-methylcyclohexyl)-methoxy)-1-propyl]-pyrrolidine
1-[2-chloro-(2.2-dimethylpropoxy)-propyl]-pyrrolidine
N-[2-chloro-(2-m thylpropoxy)-propyl]-N,N-diethylamine.

In Vitro Test Results

Rat aorta segments were suspended in an organ bath (10 ml) and connected to a force pickup, and stretched to 15 mN. The Krebs-Henseleit solution in the organ bath had the following composition:

NaCl=118 mM; KCl=4.7 mM; MgSO$_4$=1.2 mM; CaCl$_2$=2.5 mM; KH$_2$PO$_4$=1.2 mM; NaHCO$_3$=25 mM; glucose=11 mM.

The aorta segments were left in the bath for 45 minutes, to reach equilibrium, and then a stock solution of KCl was added to the organ bath to increase the KCl concentration of the nutrient solution in the organ bath to 40 mM. After the aorta segments had been exposed for 30 minutes to the increased potassium concentration, the test substances were added at an identical concentration ($10^{-6}$ mol/liter) to the bath solution. The test substances produced a relaxation effect which varied with the different test substances, and is reported in Table 1 below as a percent of the pre-contraction, determined 25 minutes after the test substance addition to the bath solution. The percent relaxation reported is a measure of the Ca++ antagonistic effect of the respective test substances. The higher the percent relaxation value reported in the right-hand column of Table 1, the more active the substance.

TABLE 1

| Compound (example) | Relaxation (%) |
|---|---|
| % relaxation following pre-contraction with 40 mM K+ ions Incubation Time: 25 minutes Concentration of the test compound: $10^{-6}$ M/liter Number of tested preparations per substance: n = 4 | |
| Bepridil | 51 |
| 3 | 67 |
| 1 | 76 |
| 4 | 59 |
| 2 | 58 |
| 8 | 71 |
| 7 | 59 |
| 10 | 65 |

TABLE 1-continued

| Compound (example) | Relaxation (%) |
|---|---|
| % relaxation following pre-contraction with 40 mM K+ ions Incubation Time: 25 minutes Concentration of the test compound: $10^{-6}$ M/liter Number of tested preparations per substance: n = 4 | |
| 11 | 68 |

Bepridil = -[2-Methylpropoxy)methyl]-N-phenyl-N-(phenylmethyl)-1-pyrrolidineethanamine. (Comparison compound of U.S. Pat. No. 3.962.238)

As will be appreciated from Table 1, the compounds of the present invention are cardiovascular agents exhibiting antianginal and antiarrhythemic properties.

The compounds of the present invention may be administered to patients in a suitable amount, generally in an amount of 50 to 1000 mg per dose. The patient will normally be administered from 1 to 3 doses daily. The total daily dosage to the patient will typically be in the range of 1 to 40 mg/kg.

We claim:

1. Compound of the formula:

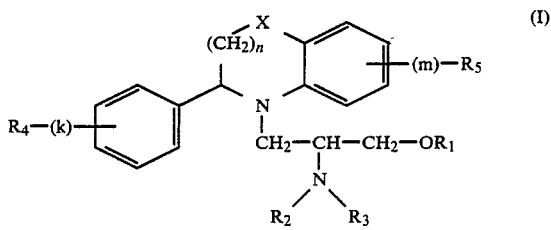

wherein $R_1$ is (a) a straight-chained or branched $C_1$–$C_{12}$-alkyl radical which is unsubstituted or substituted by at least one substituent selected from the group consisting of:
phenyl,
naphthyl, and
$C_3$–$C_7$ cycloalkyl; or $C_3$–$C_7$-cycloalkyl substituted by $C_1$–$C_4$-alkyl, (b) a straight-chained or branched $C_2$–$C_{12}$ alkenyl radical which is unsubstituted or substituted by at least one substituent selected from the group consisting of:
phenyl, and (c) a $C_3$–$C_7$ cycloalkyl radical;

(d) an aromatic radical selected from the group consisting of phenyl, naphthyl, indanyl, indenyl and tetralinyl, which aromatic radical is unsubstituted or substituted by at least one substituent selected from the group consisting of:
halogen,
carboxy,
$C_1$–$C_4$-alkoxy
$C_1$–$C_4$-alkyl,
$C_1$–$C_4$-alkoxycarbonyl; and $R_2$ and $R_3$, which can be the same or different, are straight chained or branched, saturated or unsaturated $C_1$–$C_6$-alkyl, or together with the nitrogen atom to which they are attached, form a ring selected from the group consisting of pyrrolidine, pyrroline or piperidine, piperazine, morpholine, and thiomorpholine, wherein the ring is unsubstituted or substituted by at least one substituent selected from the group consisting of:
$C_1$–$C_6$-alkyl, $C_1-C_6$-alkoxy,
hydroxyl and
an oxygen atom;

X is a methylene radical, an oxygen or sulphur atom, a sulphoxide or sulphonyl group or a $=NR_6$ group, wherein $R_6$ is hydrogen, $C_1-C_4$-alkyl or aralkyl;

n is 0, 1 or 2;

k is 0, 1, 2 or 3;

$R_4$ is halogen, hydroxyl, $C_1-C_4$ alkyl, $C_1-C_6$ alkoxy or aralkoxy, or, when k is 2, a $C_1-C_2$-alkylenedioxy radical on two adjacent carbon atoms;

m is 0, 1, 2, or 3;

$R_5$ is halogen, hydroxyl, $C_1-C_6$-alkoxy or aralkoxy; or a pharmacologically acceptable salt thereof or optical isomer thereof.

2. Compound of claim 1, wherein $R_1$ is isobutyl, isoamyl, isohexyl or neopentyl.

3. Compound of claim 1, wherein $R_1$ is cyclopentylmethyl or cyclohexylmethyl, which may be substituted by methyl, ethyl or propyl.

4. Compound of claim 1, wherein $R_1$ is allyl, methallyl, isopentenyl, hexenyl, octenyl, dodecenyl or cinnamyl.

5. Compound of claim 1, wherein at least one of $R_2$ and $R_3$ is methyl or ethyl.

6. Compound of claim 1, wherein x is oxygen, sulphur, methylene or $>NH$.

7. Compound of claim 1, wherein $R_2$ and $R_3$, together with the nitrogen atom to which they are attached, form a pyrrolidine ring.

8. Compound of claim 1, wherein at least one of $R_4$ and $R_5$ is $C_1-C_6$-alkoxy.

9. A compound of claim 1 wherein
$R_1$ is isobutyl, isoamyl, isohexyl, neopentyl, 1-methylcyclohexylmethyl, allyl, methallyl, isopentenyl, hexenyl, octenyl, dodecenyl or cinnamyl,
$R_2$ and $R_3$ each are ethyl or form together with the nitrogen atom to which they are attached a pyrrolidine ring,
X is a methylene group, an oxygen or sulphur atom or a NH group, K is 0 or 1, m is 0 or 1, n is 0 or 1, $R_4$ is methoxy and $R_5$ is methoxy.

10. Compound of claim wherein said compound is 1-[3-(2-methylpropoxy)-2-pyrrolidinopropyl]-2-phenylindoline.

11. Compound of claim wherein said compound is 1-[3-(2-methylpropoxy)-2-pyrrolidinopropyl]-2-(4-methoxylphenyl)indoline.

12. Compound of claim 1, wherein said compound is 3,4-dihydro-4-[3-(2-methylpropoxy)-2-pyrrolidinopropyl]-3-phenyl-2H-1,4-benzoxazine oxalate.

13. Compound of claim 1, wherein said compound is 3,4-dihydro-4[3-(2-methylpropoxy)-2-pyrrolidinopropyl]-3-(4-methoxylphenyl)-2H-1,4-benzoxazine.

14. Compound of claim 1, wherein said compound is 3,4-dihydro-4-[3-(3-methylbut-2-enyl-1-oxy)-2-pyrrolidinopropyl]-3-phenyl-2H-1,4-benzoxazine.

15. Compound of claim 1, wherein said compound is 3,4-dihydro-4-[3-(3-methyl-3-butenyl-1-oxy)-2-pyrrolidinopropyl]-3-2H-1,4-benzoxazine.

16. Compound of claim 1, wherein said compound is 3,4-dihydro-4-[3-(2-methylpropoxy)-2-pyrrolidinopropyl]-(3,4-methoxyphenyl)-7-methoxy-2H-1,4-benzoxazine.

17. Compound of claim 1, wherein said compound is 3,4-dihydro-4-[3-(2,2-dimethylpropoxy)-2-pyrrolidinopropyl]-3-phenyl-2H-1,4-benzoxazine.

18. Composition for the treatment of heart and circulatory diseases comprising a therapeutically effective amount of a compound of claim 1 and a pharmaceutically acceptable carrier.

19. A method of treating heart and/or circulatory diseases in a patient by relaxing blood vessels of the patient by administering to the patient a blood vessel-relaxing amount of a compound of claim 1.

20. A method of producing an antianginal and/or antiarrhythemic effect in a patient in need of such effect, said method comprising administering to said patient an effective amount of a compound of claim 1.

* * * * *